(12) United States Patent
Hu et al.

(10) Patent No.: US 11,480,674 B2
(45) Date of Patent: Oct. 25, 2022

(54) ULTRASOUND IMAGING SYSTEM WITH TRANSMIT APODIZATION

(71) Applicant: KONINKLIJKE PHILIPS N.V., Eindhoven (NL)

(72) Inventors: Changhong Hu, Bothell, WA (US); Steven Russell Freeman, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 404 days.

(21) Appl. No.: 16/516,303

(22) Filed: Jul. 19, 2019

(65) Prior Publication Data

US 2020/0025920 A1    Jan. 23, 2020

Related U.S. Application Data

(60) Provisional application No. 62/701,875, filed on Jul. 23, 2018.

(51) Int. Cl.
*G01S 7/00*     (2006.01)
*G01S 15/89*    (2006.01)
(Continued)

(52) U.S. Cl.
CPC ........ *G01S 15/8927* (2013.01); *A61B 8/4488* (2013.01); *G01S 7/52003* (2013.01);
(Continued)

(58) Field of Classification Search
CPC ............. G01S 15/8927; G01S 7/52003; G01S 7/52079; G01S 15/8952; G01S 7/52046; G01S 15/42; G01S 15/8918; A61B 8/4488
See application file for complete search history.

(56) References Cited

U.S. PATENT DOCUMENTS 4,332,171 A  *  6/1982  Iida ..................... G01S 15/8927
                                                        73/626
5,415,175 A  *  5/1995  Hanafy ................. B06B 1/0644
                                                        600/459
(Continued)

OTHER PUBLICATIONS

Lashkari, et al., "Coded excitation waveform engineering for high frame rate synthetic aperture ultrasound imaging", Ultrasonics, vol. 77, May 2017, pp. 121-132.
(Continued)

*Primary Examiner* — Isam A Alsomiri
*Assistant Examiner* — Abdallah Abulaban

(57) ABSTRACT

A digital transmit beamformer for an ultrasound system has a waveform sample memory which stores sequences of samples of different pulse transmit waveforms of differing pulse widths. The memory is shared by a plurality of transmit channels, each of which can access its own selected sample sequence, independent of the selections by other channels. Waveform sample readout by the channels occurs substantially simultaneously during a transmit event, producing a transmit beam from a transmit aperture with different pulse waveforms applied to different elements of the transmit aperture. Higher energy waveforms with wider pulse widths are applied to central elements of the aperture and lower energy waveforms with narrower pulse widths are applied to lateral elements of the aperture to produce an apodized transmit beam.

14 Claims, 5 Drawing Sheets

(51) Int. Cl.
*A61B 8/00* (2006.01)
*G01S 7/52* (2006.01)
*G01S 15/42* (2006.01)

(52) U.S. Cl.
CPC ...... *G01S 7/52079* (2013.01); *G01S 15/8952* (2013.01); *G01S 7/52046* (2013.01); *G01S 15/42* (2013.01); *G01S 15/8918* (2013.01)

(56) References Cited

U.S. PATENT DOCUMENTS

| | | | |
|---|---|---|---|
| 5,678,554 | A | 10/1997 | Hossack et al. |
| 6,043,589 | A | 3/2000 | Hanafy |
| 6,115,324 | A * | 9/2000 | Lillegard ............ G01S 7/52025 367/11 |
| 6,618,206 | B2 | 9/2003 | Tarakci et al. |
| 2004/0158154 | A1 | 8/2004 | Hanafy et al. |
| 2009/0182237 | A1 | 7/2009 | Angelsen et al. |
| 2018/0153518 | A1* | 6/2018 | Wegner ............... G01S 15/8952 |

OTHER PUBLICATIONS

Lee, et al., "Golay Codes for Simultaneous Multi-Mode Operation in Phased Arrays", 1982 Ultrasonics Symposium Proceedings, San Diego, CA, vol. 2, 1982, pp. 821-825.

* cited by examiner

ULTRASOUND IMAGING SYSTEM WITH TRANSMIT APODIZATION

RELATED APPLICATION

The present application claims priority to and the benefit of U.S. Provisional Application No. 62/701,875, filed on Jul. 23, 2018, which is hereby incorporated by reference herein in its entirety.

This invention relates to ultrasound imaging systems and, in particular, to a digital transmit beamformer for an ultrasound system which stores selectable sequences of digital samples of transmit waveforms and provides transmit apodization.

Ultrasound systems which use multi-element array transducers employ beamformers to steer and focus the beams transmitted by and echoes received by the transducer arrays. Transmission is done by applying transmit signals to the elements of the array which are respectively delayed so that the resultant beam is steered in a desired direction and is focused at a desired focal point along the beam. The received echo signals are respectively delayed and then summed to produce a sequence of coherent echo signals from the beam direction from shallow to deeper depths. Originally beamformers were entirely analog and used analog components to delay, transmit, receive and process the transmitted beams and the received echo signals. The evolution of the beamformer since then has been marked by increasing digitization. The concepts of a digital receive beamformer appeared in the patent literature in the 1970s as exemplified by U.S. Pat. No. 4,301,501 (Caruso) and U.S. Pat. No. 4,173,007 (McKeighen et al.) Commercial ultrasound systems with digital receive beamformers began to appear on the market in the 1980s. The concepts of a digital transmit beamformer appeared in the patent literature in the early 1990s as illustrated by U.S. Pat. No. 4,893,629 (Lewis). Commercial ultrasound systems with digital transmit beamformers appeared later in the 1990s. Subsequently, ultrasound systems implemented transmit beamformers capable of creating simultaneous transmit beams at different spatial locations using apodization as illustrated by U.S. Pat. No. 6,066,099 (Thomenius et al.) Other patents proposed using different transmit frequencies along spatially separate beams (e.g., U.S. Pat. No. 6,159,153, Dubberstein et al.) to better isolate signals received simultaneously from tissue at multiple positions. Even more recently, weakly focused, plane-wave, and defocused transmit beams have been proposed in U.S. Pat. No. 6,551,246 (Ustuner et al.) and in the literature, e.g., "Architecture of an Ultrasound System for Continuous Real-Time High Frame Rate Imaging", Boni et al., IEEE Trans. on Ultrason., Ferroelec., and Freq. Control, vol. 64, no. 9 (2017); and "Multi-transmit Beam Forming for Fast Cardiac Imaging," Tong et al., IEEE Int'l Ultrason. Sympos. Proc., (2011).

Early ultrasound systems relied upon a simple pulser to excite the transducer elements into acoustic transmission. An electrical pulse would be applied to an element at the appropriate time for its contribution to the desired beam formation, causing the transducer element to vibrate and generate an acoustic pulse at its resonant frequency. Pulsed transmission produces broadband energy, which is desirable for imaging modes such as B mode, but other modes such as Doppler modes are more effective with narrower band transmission. Narrow band transmission requires longer, oscillatory waveforms for optimal frequency selectivity. As the Lewis patent illustrates, the essence of a digital transmit beamformer is a digital memory which stores a sequence of digital samples of a transmit waveform. The value of each digital word defines the amplitude of the waveform at a particular point in time, and the rate at which the words are read from the memory defines the shape and frequency content of the transmitted waveform. Thus, the sequence of digital waveform samples can define a complex waveform such as an oscillating waveform. Since transducer array elements are by nature analog devices, the digital words delineating the transmit waveform are not directly applied to the transducer elements, but are converted to an analog waveform by a digital-to-analog converter. The analog waveform is then amplified and applied to an element of the transducer array. By applying the analog waveform to different transducer elements at different times, which effects the delays of a beamformer, the array produces a beam which is steered in a given direction and focused at a desired depth, with the desired frequency content.

Ultrasound systems can employ apodization across the aperture on both transmit and receive. A principal reason for using apodization is to reduce sidelobes in the acoustic beam pattern and consequently their off-axis artifacts. The conventional way to modify a transmit or receive signal for apodization is to weight it with an apodization function. Different weights are used in different channels across the aperture. Such weighting is done by multiplying individual transmit or received signals by weighting values, which requires multipliers or similar processors in the beamformer signal paths. It would be desirable to be able to perform apodization without the need for this additional hardware or software, and to eliminate the time required to perform these operations.

In accordance with the principles of the present invention, a digital transmit beamformer for an ultrasound system has the capability of selectively transmitting different pulsed or linear waveforms on a line-by-line basis. In a preferred implementation the choice of the transmit pulse or waveform can even be made on a channel-by-channel basis, enabling different elements within the active aperture to transmit different signals for a common transmit beam. By applying different signals to different elements of a transmit aperture, transmit apodization is provided. In a preferred implementation, the different signals are pulse waveforms shaped by pulse width variation so as to provide different transmit energies from elements of the transmit aperture.

Figure 1:
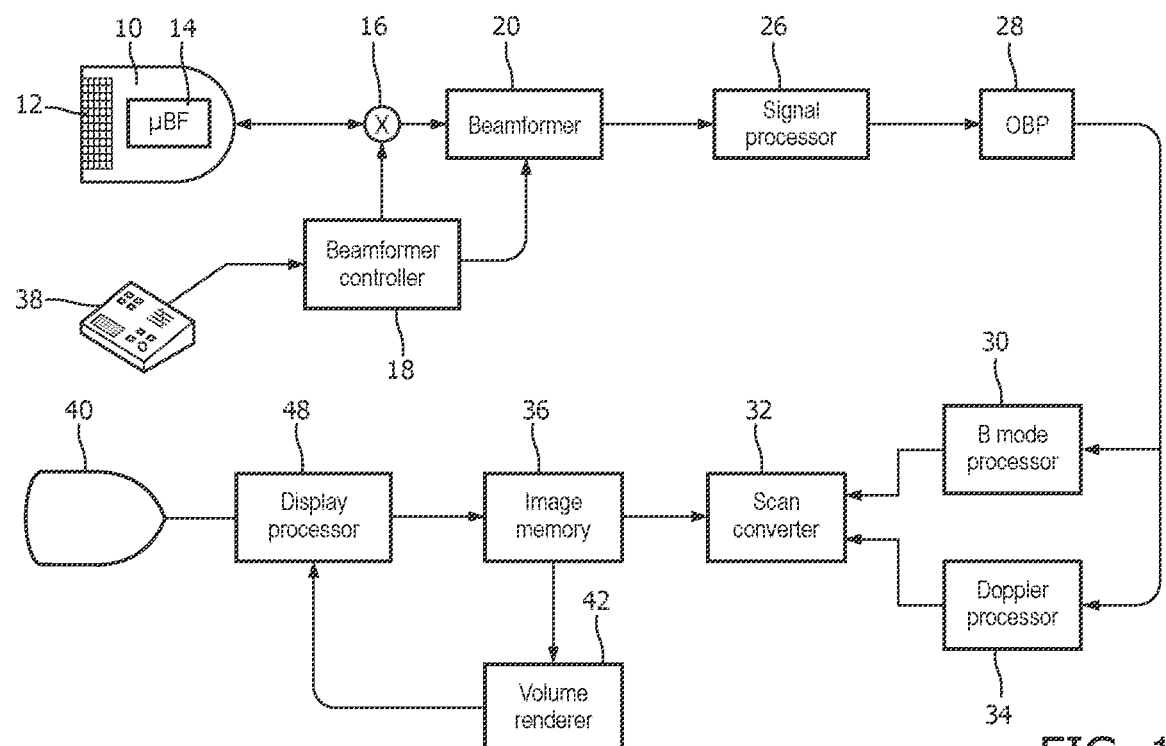
FIG. 1 illustrates in block diagram form an ultrasound system configured in accordance with the principles of the present invention.

Referring now to FIG. 1, an ultrasonic diagnostic imaging system constructed in accordance with the principles of the present invention is shown in block diagram form. A transducer array 12 is provided in an ultrasound probe 10 for transmitting ultrasonic waves and receiving echo information. The transducer array 12 may be a one- or twodimensional array of transducer elements capable of scanning in two or three dimensions, for instance, in both elevation (in 3D) and azimuth. The transducer array 12 can be coupled to a main beamformer, or as shown an optional microbeamformer 14 in the probe which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The main beamformer or the microbeamformer can be coupled by the probe cable to a transmit/receive (T/R) switch 16 which switches between transmission and reception. A reconstruction filter is also included (in the connector?) between the T/R switch and the beamformer or microbeamformer. This reconstruction filter can convert the 'digital' PWM to an analog voltage that the main beamformer or microbeamformer can appropriately sample. The transmission of ultrasonic beams from the transducer array 12 under control of the main beamformer 20 or microbeamformer 14 is directed by a beamformer controller 18, which receives input from the user's operation of the user interface or control panel 38. Among the transmit characteristics controlled by the transmit controller are the number, spacing, amplitude, phase, frequency, polarity, and diversity of transmit waveforms. Beams formed in the direction of pulse transmission may be steered straight ahead from the transducer array, or at different angles on either side of an unsteered beam for a wider sector field of view. For some applications, unfocused plane waves may be used for transmission, and in this case the receive beams may interrogate the entire field of view simultaneously. Most 1D array probes of relatively small array length, e.g., a 128-element array, do not use a microbeamformer but are driven and respond directly to the main beamformer.

The echoes received by a contiguous group of transducer elements are beamformed by appropriately delaying them and then combining them. The coherent echo signals undergo signal processing by a signal processor 26, which includes filtering by a digital filter and noise reduction as by spatial or frequency compounding. The filtered echo signals are coupled to a quadrature bandpass filter (QBP) 28. The QBP performs three functions: band limiting the RF echo signal data, producing in-phase and quadrature pairs (I and Q) of echo signal data, and decimating the digital sample rate. The QBP comprises two separate filters, one producing in-phase samples and the other producing quadrature samples, with each filter being formed by a plurality of multiplier-accumulators (MACs) implementing an FIR filter. The quadrature signal samples undergo signal processing by a signal processor 16, which includes filtering by a digital filter and speckle reduction as by spatial or frequency compounding. The signal processor can also shift the frequency band to a lower or baseband frequency range, as can the QBP. The digital filter of the signal processor 26 can be a filter of the type disclosed in U.S. Pat. No. 5,833,613 (Averkiou et al.), for example.

Figure 3:
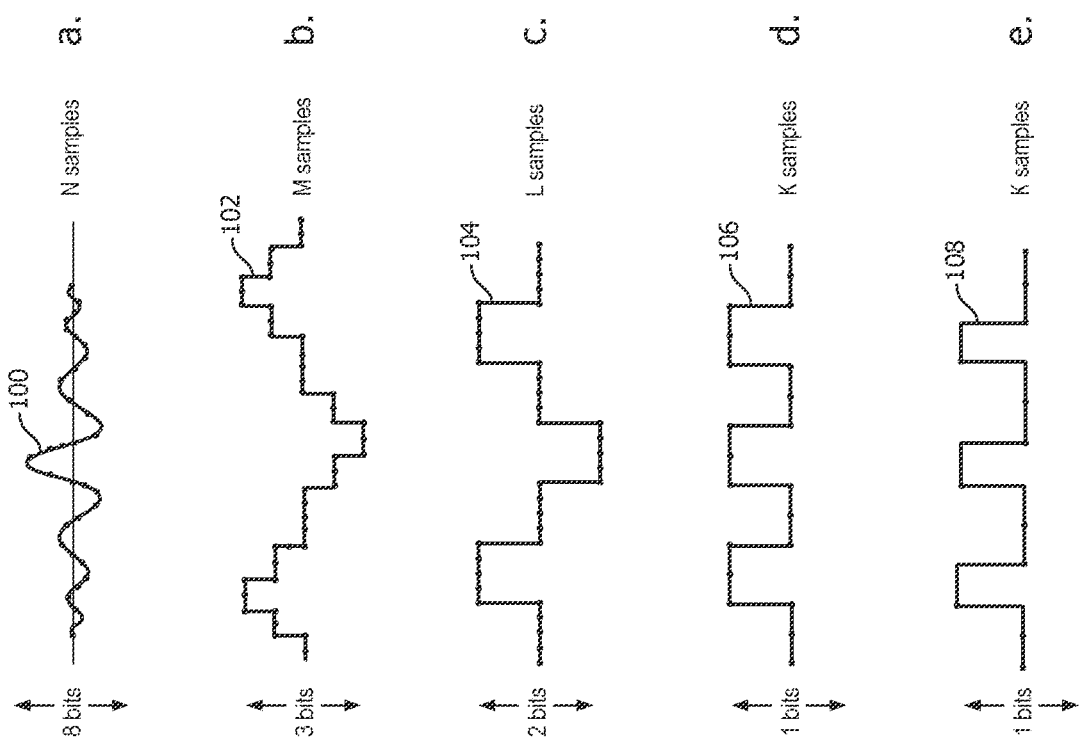
FIG. 3 shows examples of some of the linear and pulse waveform types which may be transmitted by the digital transmit beamformer of FIG. 2.

The beamformed and processed coherent echo signals are coupled to a B mode processor 30 which produces a B mode image of structure in the body such as tissue. The B mode processor performs amplitude (envelope) detection of quadrature demodulated I and Q signal components by calculating the echo signal amplitude in the form of $(I^2+Q^2)^{1/2}$. The quadrature echo signal components are also coupled to a Doppler processor 34. The Doppler processor 34 stores ensembles of echo signals from discrete points in an image field which are then used to estimate the Doppler shift at points in the image with a fast Fourier transform (FFT) processor. The rate at which the ensembles are acquired determines the velocity range of motion that the system can accurately measure and depict in an image. The Doppler shift is proportional to motion at points in the image field, e.g., blood flow and tissue motion. For a color Doppler image, the estimated Doppler flow values at each point in a blood vessel are wall filtered and converted to color values using a look-up table. The wall filter has an adjustable cutoff frequency above or below which motion will be rejected such as the low frequency motion of the wall of a blood vessel when imaging flowing blood. The B mode image signals and the Doppler flow values are coupled to a scan converter 32 which converts the B mode and Doppler samples from their acquired R-θ coordinates to Cartesian (x,y) coordinates for display in a desired display format, e.g., a rectilinear display format or a sector display format. Either the B mode image or the Doppler image may be displayed alone, or the two shown together in anatomical registration in which the color Doppler overlay shows the blood flow in tissue and vessels in the image as shown in FIGS. 3a-3c. Another display possibility is to display side-by-side images of the same anatomy which have been processed differently. This display format is useful when comparing images.

The image data produced by the B mode processor 30 and the Doppler processor 34 are coupled to an image data memory 36, where it is stored in memory locations addressable in accordance with the spatial locations from which the image values were acquired. Image data from 3D scanning can be accessed by a volume renderer 42, which converts the echo signals of a 3D data set into a projected 3D image as viewed from a given reference point as described in U.S. Pat. No. 6,530,885 (Entrekin et al.) The 3D images produced by the volume renderer 42 and 2D images produced by the scan converter 32 are coupled to a display processor 48 for further enhancement, buffering and temporary storage for display on an image display 40.

Figure 2:
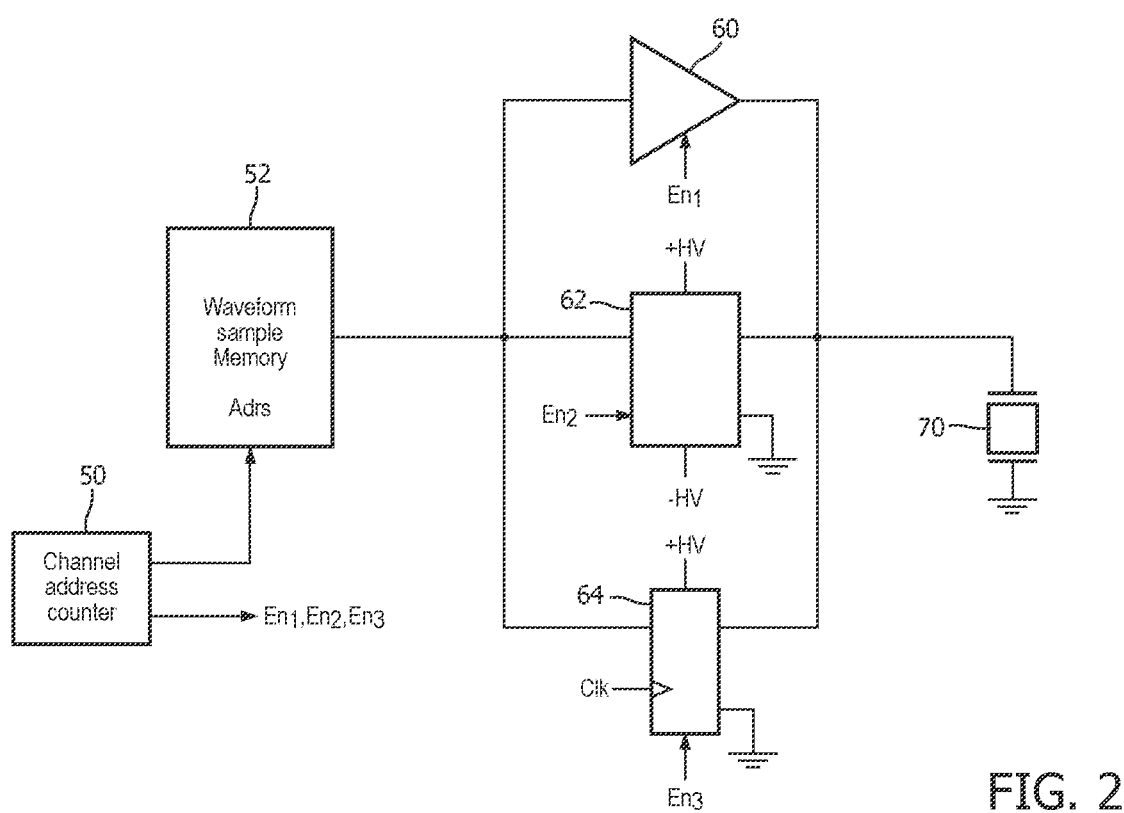
FIG. 2 illustrates in block diagram form a digital transmit beamformer of the present invention suitable for use in the ultrasound system of FIG. 1.

In accordance with the principles of the present invention, the beamformer 20 includes a digital transmit beamformer which is capable of actuating elements of a transducer array in probe 10 with either linear waveforms or transmit pulses. FIG. 2 illustrates a channel of a digital transmit beamformer of the present invention in block diagram form. Digital samples of linear and pulse waveforms for transmission in both transmit modes are stored in a waveform sample memory 52. The digital samples may be acquired for the memory 52 by digitally sampling a desired analog transmit waveform with an analog to digital converter. The sample rate of the analog to digital converter should satisfy the Nyquist criterion for sampling by sampling at a frequency which is at least twice that of the highest frequency component of the waveform. Higher sampling rates can be desirable in some implementations. A waveform may be produced by a waveform generator and sampled, for instance, or a waveform may be constructed in the frequency domain and then converted to the time domain for sampling by an inverse Fourier transform. Transmit pulse sequences may be constructed directly in digital form without the need for conversion by producing digital words of one, two, or three bits in accordance with the desired number of pulse levels and in consideration of a clock rate which will cause level transitions in a sequence of samples to occur at the desired times. Other techniques for generating transmit waveforms are well known to those skilled in the art.

A sequence of digital samples, which defines either a linear (e.g., shaped sinusoid) waveform or a pulse sequence, is stored in the memory in sequential memory locations.

This enables the sequence to be read out in sequential order by addressing the memory with a read address counter 50, as shown in the drawing. The clock rate at which the samples are read out is chosen in consideration of the frequency of the desired waveform. For example, a pulse sequence can be read out at a low clock rate to produce a sequence of long, low frequency pulses, or the same sequence can be read out at a higher clock rate to produce a sequence of more narrow, higher frequency pulses. The same is true when reading out a linear sinusoidal waveform.

A sequence of samples which is read out of the memory 52 is applied to three types of waveform and pulse transmitters in this example, a digital to analog converter 60, a two-level pulser 64, and a higher multi-level pulser 62 which can produce a pulse sequence of three, four or five levels. The transmitter comprises an individual set of these output devices for each channel of the transmit beamformer, with the outputs of the devices coupled to a transducer element 70. An enable signal, $En_1$, $En_2$, or $En_3$, from the channel address counter 50 enables the appropriate output device for that channel. The converter 60 will convert a sequence of digital words into a linear waveform such as the one shown in FIG. 3a. In this example each digital word is an eight-bit word and the word value defines the instantaneous amplitude as one of 256 possible levels. Each dot on the linear waveform 100 represents an eight-bit waveform sample, and the conversion of the digital word sequence to analog levels produces a linear waveform such as the one shown in the drawing. In this example, the analog waveform 100 is produced by digital to analog conversion of a sequence of N digital samples.

The two-level pulser 64 operates in the manner of a D-type flip-flop, with the clock Clk producing an output at the level of the digital word applied to the data input of the pulser. While different size digital samples can be employed, a two-level device only requires the digital sample to be a single bit, which will have either a one or zero value. When the sequence of bits changes from a zero to a one, the clock will transition the output to the high state of a pulse, which will remain high until the input bit sequences changes back to a zero. Transitions of the output pulse sequence will occur in phase with the clock signal. A typical two-level output pulse train 106 produced by the two-level pulser 64 is shown in FIG. 3d. In most instances, lower frequency read-out addressing by the channel address counter is also possible. With fewer samples needed to define the pulse train, and those samples being as small as one bit, fewer memory location of memory 52 are needed to store the digital samples for a two-level pulse. A large number of pulse train sequences can be stored in the same memory space required for one linear waveform of eight-bit words.

The multi-level pulser 62 produces a multi-level pulse train such as pulse trains 102 and 104 shown in FIGS. 3b and 3c. Pulser 62 can be constructed using a digital decoder driving stacked, oppositely poled switching transistors which are coupled to voltage supplies for the pulse levels. A three-level pulse train 104 as shown in FIG. 3c can require only two voltage levels (+HV and –HV) as shown in FIG. 2, which will produce a pulse train such as 104 with a high (+HV), low (–HV) and intermediate (reference or ground) pulse level. A three-level pulse can be defined by two bits for the three levels, and the digital decoder can be as simple as a two-bit register into which the two-bit samples are sequentially loaded to drive the switching transistors.

For pulse trains of five, six or seven levels, additional supply voltage levels are required. The five-level pulse train 102 in FIG. 3b, for instance, can be produced using two positive voltage supplies (+HV and ++HV) and two ground or negative supplies (–HV and ––HV), for instance. Three-bit words are necessary to define the five possible pulse levels, which can be decoded into the five signals necessary to drive the switching transistors, for example. Like the two-level pulse train of FIG. 3d, the digital sample sequences for the three- and five-level pulse trains 104 and 102 need fewer sample words than are needed for the linear waveform 100, and those words are of a lesser number of bits, meaning that they, too, require fewer memory storage locations than does the sample sequence for the linear waveform 100. The K, L, and M sample sequence lengths will generally be less than the N sample sequence needed for the linear waveform.

The beamformer transmitter shown in FIG. 2 can drive a transducer element 70 with either a linear or a pulse transmit waveform, depending upon which stored pulse or waveform sequence is read from the memory 52 by the channel address counter 50, and which output device 60, 62 or 64 is enabled by an enable signal. FIG. 2 shows the components for one channel of a beamformer transmitter, with each element or patch of an array transducer driven by its own transmit channel. Thus, each transmit beamformer channel is characterized by its own set of output devices and its own channel address counter.

In accordance with a preferred implementation of the present invention, a plurality of channels share the same waveform sample memory. That is, the linear and pulse samples for multiple channels and multiple transducer elements are stored and read from a common waveform memory. Furthermore, the selection of a transmit waveform by one channel address counter for one transducer element is independent of the choices of transmit waveforms by the other channel for the other transducer elements. Thus, the active transmit aperture used to produce a transmit beam can, if desired, transmit different waveforms or pulses from different elements during the same transmit event. Moreover, many, and possibly all, of the channel address counters of the channels of the active transmit aperture are reading out their transmit waveform sequences from the waveform sample memory at the same time.

Figure 4:
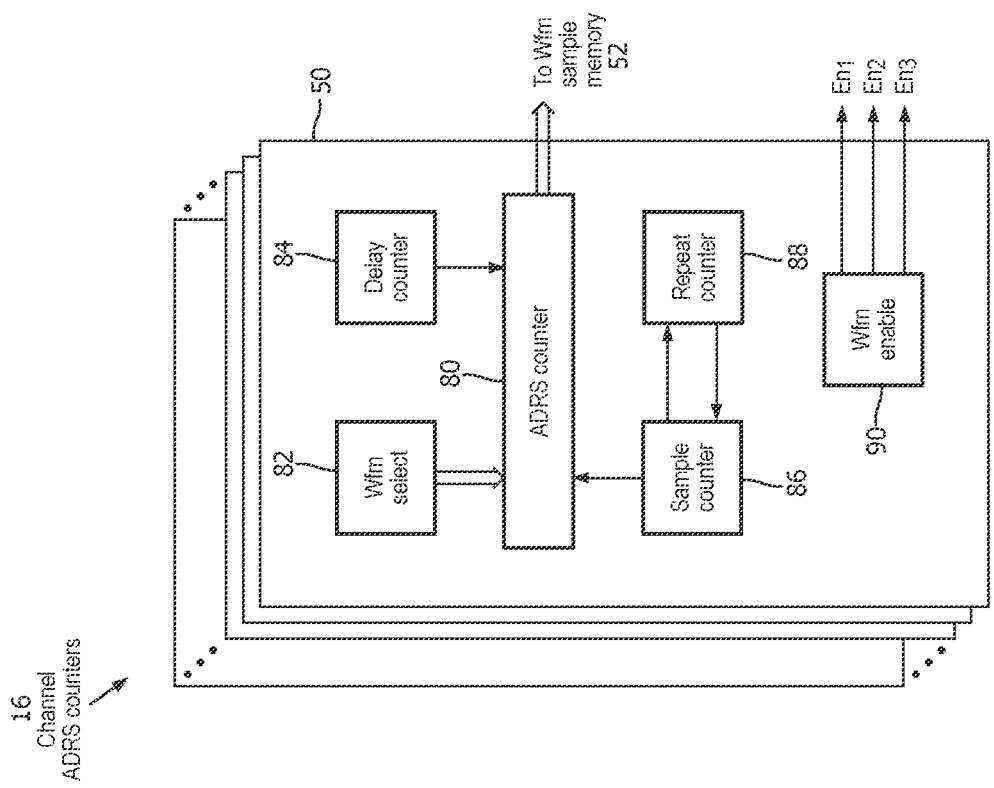
FIG. 4 illustrates the channel address counter of the digital transmit beamformer of FIG. 2 in further detail.

How this is done is shown in further detail in the illustration of the bank of channel address counters 50 shown in FIG. 4. This drawing shows a group of sixteen channel address counters 50 which are fabricated with a shared waveform sample memory 52 on one ASIC integrated circuit. An address counter 80 of each channel address counter is coupled to address lines of the shared waveform sample memory 52. A sequence of samples for a desired waveform is addressed by the counter, starting with a starting address and counting through the consecutively addressed samples until all of the samples for the waveform are read out. The starting address for the sequence of samples is initially loaded into the address counter 80 from a waveform select register 82. In order to steer and focus the transmit beam from an active transmit aperture of transducer elements, the times of transmission by each channel must be phased, or delayed, by a delay profile appropriate for the beam steering and focusing. This requires the start of transmission by each element to be uniquely delayed in accordance with the delay profile. In the special case of an unsteered beam, that is, one which is transmitted normal to the face of the array, the beam profile is symmetrical and elements equidistant on either side of the beam center will exhibit the same delay. In other instances, each channel will have its own delay for combined steering and focusing. The delay for a channel is implemented by a delay counter 84, which is initially loaded with a delay count appropriate for the delay required in that channel. A transmit synchronization signal, issued by a common controller for all of the channels, actuates the delay counters 84, each of which begins to count down the delay for its channel. When a delay counter reaches zero, the appropriate delay for the channel has expired and the delay counter 84 enables its address counter 80 to begin to count and issue consecutive addresses for the digital sample words of the waveform. As previously mentioned, the counting begins with the proper starting address for the sequence of samples to be transmitted. The counting of samples is controlled by a sample counter 86, which has been previously loaded with the number of samples comprising the sample sequence. When counting is enabled by the delay counter 84, the sample counter 86 begins to count down, with each count incrementing the address counter by another bit. Thus, the address counter produces a sequence of consecutive sample memory addresses, beginning with the starting address of the desired sample sequence for that particular channel, and continues to issue consecutive addressed to the waveform memory until the sample counter has counted the required number of samples of the sequence. When the sample counter reaches zero, counting and incrementing of the address counter stops, as the entire required sample sequence has been read from the memory.

An optional repeat counter 88 is coupled to the sample counter. The purpose of the repeat counter is to cause the sample counter and address counter to read out the same sequence of samples again. This enables production of a longer waveform by successively reading out a number of shorter waveforms. For example, suppose that a particular sample sequence defines one cycle of a transmit waveform. Further suppose that it is desired to transmit a three-cycle waveform. The repeat counter will cause the address counter and its associated components to address the same one-cycle sample sequence three times in succession, thereby producing a three-cycle waveform for transmission. In this example the repeat counter is initialized with a count of three, and when it reaches zero all three cycles will have been read from the waveform memory and memory addressing by the channel ends.

Each channel address counter 50 also includes a waveform enable register or decoder 90. This device is loaded with a digital word prior to transmission which enables the desired output device 60, 62, or 64 for transmission by that channel. The waveform enable word may be a three-bit word of a binary value of either 001, 010, or 100 which, when loaded into a register, will produce a high signal on one of three output lines for enable control. Alternately, the waveform enable device may be a two-bit decoder for the three enabling output lines.

A simple example will illustrate the sequencing and interaction of the components of a channel address counter and the sample waveform memory. Suppose that there are 256 samples in memory for a waveform which is to be transmitted by a particular transducer element, and that this sequence of samples is stored in sequence beginning at memory address 1024. Further suppose that transmission by the transducer element is to be delayed by the time of 100 clock cycles of the clock which increments the delay counter 84. This channel address counter is initialized by loading the starting memory address of 1024 into the address counter from the waveform select register 82, loading the delay counter 84 with the delay time of 100, loading the sample counter 86 with the sample sequence length of 256, and loading the repeat counter with a repeat count of one. When the transmit synchronization signal is received from a central or common controller, the delay counter 84 begins counting down from 100. When the delay counter reaches zero, the sample counter 86 is enabled and begins to count down from 256, incrementing the address counter which issues consecutive memory addresses to the waveform sample memory, beginning with the starting address of 1024. When the sample counter reaches zero, at which time the full waveform of 256 samples has been read from memory, the sample counter decrements the repeat counter 88 from one to zero. The zero value from the repeat counter halts the sample counter, and waveform sample readout is complete. Thus, following a delay time of 100 delay clock cycles, the desired waveform of 256 samples has been read from memory and transmitted by the transducer element. The other channels for the active transmit aperture are functioning in the same way, using the same or different starting addresses for their waveform sample sequences, so that pulse or linear waveforms for a plurality of transducer elements are provided concurrently by the waveform sample memory for the same transmit event. The transmitter can also control the timing of these enabled devices relative to the transmit waveform. The transmit/receive (TR) switch, for example, may not open and close instantaneously, so a control signal can be provided to the TR switch to open before the transmit waveform starts. Likewise, the linear transmitter may also need time to power-up and later power-down before and after the waveform.

Previous efforts toward digital transmit beamformers have tried to use various shortcuts in attempts to reduce memory size requirements. All of these approaches have, in various ways, limited transmitter performance, increased hardware or software complexity, or suffered combinations of these effects. A conventional approach has been to provide each channel with its own waveform memory. If the same waveform is to be used by multiple channels, it must be stored in the memory of each channel with this approach. A common, shared memory makes more efficient use of memory storage space. Another proposal is to store waveform samples for two waveforms as halves of double words in memory, so that half of a readout word is used for one waveform and the other half is used for another waveform. This necessarily requires the two waveforms to be used for the same transmission, preventing each channel from selecting a waveform independently of the other. It also requires different delays for the two waveforms to be applied in subsequent processing. Another proposal has been to read out samples for two waveforms in interleaved fashion, ping-ponging back and forth between the two waveforms. This approach mandates redirecting the samples into two paths for the two waveforms, and also halves the high frequency resolution of the resultant transmit beams since the waveform sample rate is cut in half, a problem which can be overcome by doubling the read speed, which may not be feasible or desirable. Yet another approach has been to store only the envelope of the transmit waveform, and subsequently modulate the envelope with a high frequency carrier. This requires a modulator to be implemented and operate before a waveform can be transmitted. Still another approach is to store only a few waveforms in memory, then perform interpolations of them to generate additional waveforms. This requires a waveform interpolator to be implemented and operate before a waveform can be transmitted. Other approaches have called for storing one or only a few waveforms in memory, then weighting or phasing them or adding successive waveform increments to generate the additional required waveforms. Again, additional hardware or software is needed to perform these operations, and the time required to execute them before transmission must be figured into the waveform production time. And the delays must be implemented in a subsequent operation. A preferred implementation of a transmit beamformer of the present invention avoids all of these deficiencies and complexities by allowing each channel to address a desired waveform in memory independently of the selections by other channels. This independent operation of the transmit channels is made possible by having all channel address counters on an ASIC share a common waveform sample memory, which all of the channels can access simultaneously and independently. Since the channel address counters and their common memory are all on the same integrated circuit, all address bus routing is done on the IC so that no IC pins are needed for waveform sample addressing. The implementation of FIG. 4 shows sixteen address counters which, together with their waveform sample memory, are fabricated on the same ASIC. Thus, eight of these ASICs will support a 128-element array requiring 128 transmit channels. Higher integration is also possible and desirable. When 32 or 64 or 128 channel address counters and their shared memory are fabricated on the same ASIC, only four, two or one such transmit ASIC is required to support a 128-element array.

Figure 5:
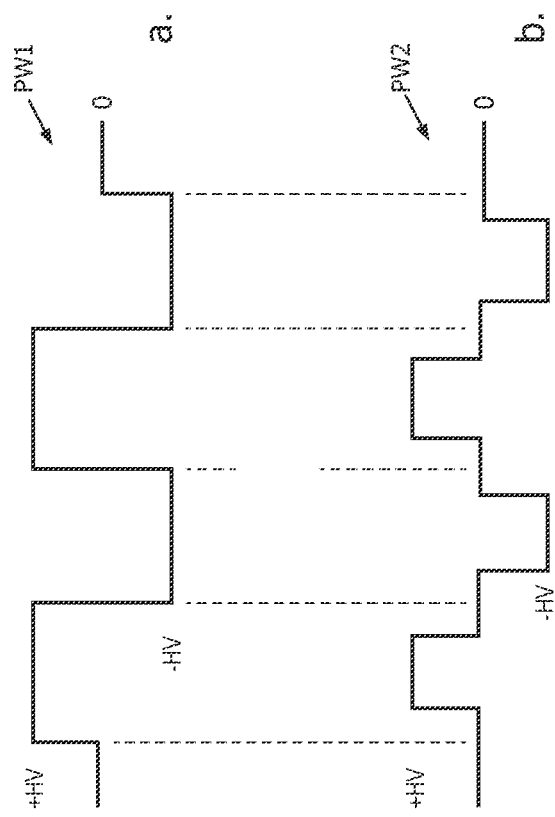
FIG. 5 illustrates two pulse waveforms which provide transmit apodization.

The capability of each channel of a digital transmit beamformer to select one of a plurality of waveform or pulse train sample sequences in memory, independently of the other channels, enables the beamformer to transmit a beam from an active aperture in which different elements transmit different waveforms. Conventional beamformers transmit the same pulse train or waveform, with appropriate delays, from each element of the transmit aperture. The constructive and destructive interference of wavefronts in an image field scanned with a single transmit waveform are well understood and accepted. But the ability to transmit different signals from different elements of the aperture enables additional imaging features to be obtained. One such application of the use of different transmit waveforms to produce a beam with a line focus, whereby different frequencies are focused at different depths. Examples of this application are described in a concurrently filed patent application by the present inventors. Another application is to use different waveforms to drive different elements in a transmit aperture for transmit apodization. As mentioned above, apodization is conventionally performed by multiplying the transmit pulse or waveform by an apodization weighting factor, with the signals for central elements of the aperture being weighted most strongly. This calls for a weighting circuit for the signal of each element which weights the transmit signals before they are applied to the array elements. But the present inventors have recognized that different waveforms can apply different levels of energy to different transducers, and that this phenomenon can be used to produce an apodization effect. Accordingly, the waveforms stored in memory for different elements for an apodized transmission are of different transmit energies. For linear waveforms this is readily accomplished by storing waveform samples of different sample word values. With an 8-bit word providing 256 increments of amplitude resolution, scaling the waveform samples to scale the amplitude of the transmitted linear waveform is a straightforward process. Pulse waveforms, however, are constrained by the system transmit voltage levels. A three-level pulse, for instance, can only have three possible levels: +HV, zero, and −HV determined by the power supply voltage levels. In accordance with the principles of the present invention, the inventors tailor the energy of pulse waveforms by pulse width variation. Pulse width modulation is known in the literature for its use in replicating modulated analog waveforms as described, for instance, in "Width-Modulated Square-Wave Pulses for Ultrasound Applications" by Smith et al., IEEE Trans. on Ultrason., Ferroelec., and Freq. Control, vol. 60, no. 11, (November 2013). FIG. 5 provides an example of two such three-level pulse waveforms. Pulse waveform PW1 in FIG. 5a is seen to have four pulses of positive and negative excursions which vary between zero, +HV in the positive direction, and −HV in the negative direction. The areas under the pulses between the positive and negative excursions and the reference level is seen to provide a certain amount of pulse energy. The pulse waveform PW2 in FIG. 5b is seen to also exhibit four pulses and of the same fundamental frequency. But the pulses of pulse waveform PW2 are seen to be narrower than the corresponding pulse excursions of PW1, as is evident from the dashed lines between the two pulse waveforms. Thus, less energy is provided by the PW2 pulses, as evident from the smaller area under the pulses between the pulse excursions and the reference level. This transmit energy difference allows the two pulse waveforms to be used in an apodized transmission of these three-level pulses.

Figure 6:
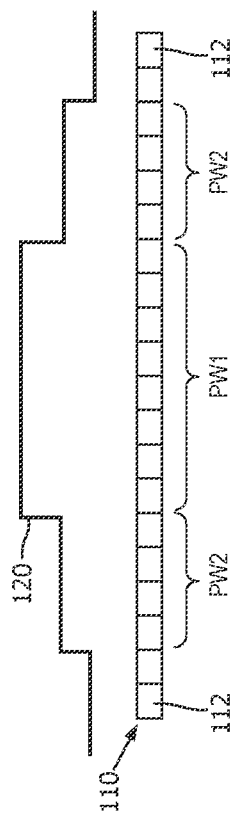
FIG. 6 illustrates an apodization function created when the pulse waveforms of FIG. 5 are applied to an array transducer.

FIG. 6 illustrates use of the two pulse waveforms of FIG. 5 to provide an apodized transmission from a transmit aperture of a linear array. The linear array 110 is comprised of twenty transducer elements 112 in this example, and are used as the transmit aperture for pulse transmission. The eight central transducer elements are driven by applying pulse waveform PW1 to the elements, with appropriate delays for beam steering and focusing. This is indicated by the PW1 bracket. The four elements on either side of these central element are driven by applying pulse waveform PW2 to those elements, as indicated by the PW2 bracket. The two elements on the two ends of the aperture are not actuated. This causes the central elements to be driven with high energy, the four elements to either side of the central elements to be driven with lower energy, and the elements on either end to be driven with even lower (i.e., zero) energy. The apodization function thereby applied to the transmit aperture is shown as the characteristic 120, which steps from a higher central level to a lesser level on either lateral side, and finally to a base level. Apodization is thus accomplished without the need for circuitry or software to weight the twenty element signals prior to beam transmission.

An even simpler example of pulse transmit waveforms of different pulse widths and hence different transmit energies is illustrated by the pulse transmit waveforms of FIGS. 3d and 3e. Pulse transmit waveform 106 is a sequence of pulses of a wider pulse width and thus higher transmitted energy, and pulse transmit waveform 108 is a sequence of pulses of a narrower width and thus lower transmitted energy, and the pulses of both recur at the same fundamental frequency. Since the pulse sequences only have two levels, their digital word size only needs to be a single bit of zero or one for the two levels of the pulse. These pulse sequences can be transmitted by a two-level pulse transmitter having only a unipolar power supply, i.e., +HV and reference or ground level. A sequence of single-bit words can be stored efficiently in the waveform sample memory. A simple example illustrates the efficiency of using the digital transmitter of FIG. 2 to transmit pulse width modulated waveforms rather than pulse width modulation circuitry for each transmit channel. Not only is there no need for additional circuitry, but the pre-stored digital samples use very little memory storage. For example, with the digital data sequences used to transmit the two waveforms of FIGS. 3d and 3e, the sequences can be:

00000111110000011111000001111100000 and
00000011100000001110000000111000000

Thus, each waveform is a sequence of thirty-five 1-bit words, with a total of only 35 bits required for each sequence, a very small memory allocation. Multiple sequences of different pulse widths can be stored with a very small memory requirement. This is a much more economical alternative than pulse width modulation circuitry for each channel as used in the prior art, and more efficient than using an A/D converter and linear amplifier which, for eight-bit words, would require a memory allocation of 280 bits. Three-level pulses such as those of FIG. 5 can use 3-bit words, a total of 105 bits for each pulse sequence of the same word length.

Other examples of using an implementation of the present invention to independently control the transmit signals of the elements of a transmit aperture will readily occur to those skilled in the art. It may be desirable to reduce the occurrence of grating lobe artifacts in an image by transmitting higher frequency signals from one side of the transmit aperture and lower frequency signals from the other side when a beam is steered off-axis, for instance.

It should be noted that an ultrasound system suitable for use in an implementation of the present invention, and in particular the component structure of the ultrasound system of FIGS. 1, 2, and 4, may be implemented in hardware, software or a combination thereof. The various embodiments and/or components of an ultrasound system, for example, the channel address counter and its controller, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as the waveform sample memory 52 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and display of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as a transmit control module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. A beamformer system for providing transmit apodization in an ultrasound system, comprising:
   a digital memory adapted to store digital samples of a plurality of linear or pulse transmit waveforms,
   a plurality of channel address counters, coupled to the digital memory, each adapted to address a sequence of digital samples of a transmit waveform stored in the memory independently of addressing a digital sample sequence by other channel address counters in the plurality,
   a plurality of transmitter output devices, coupled to the digital memory that are responsive to a sequence of digital waveform samples and adapted, when enabled, to produce a pulse or linear waveform for an array of transducer elements, and
   an array of transducer elements that are each coupled to an output of one or more of the plurality of transmitter output devices and adapted to produce an ultrasound beam from a transmit aperture when actuated by a pulse or linear waveform,
   wherein the plurality of channel address counters are further adapted to address different sequences of digital samples of different transmit waveforms stored in the digital memory, and
   wherein the plurality of transmitter output devices are further adapted to transmit different waveforms from different elements of the transmit aperture during a common transmit event.

2. The beamformer system of claim 1, wherein the digital memory is further adapted to store digital samples of a plurality of pulse transmit waveforms of different transmit energies for transmission during the common transmit event.

3. The beamformer system of claim 2, wherein the plurality of channel address counters are further adapted to address a sequence of digital samples of a pulse transmit waveform of a higher energy for transmission by central elements of the transmit aperture, and to address a sequence of digital samples of a pulse transmit waveform of a lower energy for transmission by elements lateral of central elements of the transmit aperture.

4. The beamformer system of claim 3, wherein the transmit aperture is characterized by an apodization function across the transmit aperture which is higher in the center and lower at ends of the transmit aperture.

5. The beamformer system of claim 2, wherein the pulse transmit waveforms differ by pulse width variation.

6. The beamformer system of claim 5, wherein pulse transmit waveforms of a wider pulse width are configured to produce a higher transmit energy, and wherein pulse transmit waveforms of a narrower pulse width are configured to produce a lower transmit energy.

7. The beamformer system of claim 1, wherein the array of transducer elements further comprises a row of transducer elements configured to exhibit an active transmit aperture such that higher energy transmit waveforms are applied by the transmitter output devices to central elements of the active transmit aperture and lower energy transmit waveforms are applied to elements on either side of the central elements of the active transmit aperture.

8. The beamformer system of claim 1, wherein the digital memory is further adapted to store digital samples of a plurality of pulse transmit waveforms of different pulse widths,
wherein the array of transducer elements further comprises a row of transducer elements configured to exhibit an active transmit aperture, and
wherein the transmitter output devices are further adapted to apply pulse transmit waveforms of a wider pulse width to central elements of the active transmit aperture and to apply pulse transmit waveforms of a narrower pulse width to elements on either side of the central elements of the active transmit aperture.

9. The beamformer system of claim 8, wherein the plurality of transmitter output devices comprise pulse waveform transmitters.

10. The beamformer system of claim 9, wherein the digital samples of a pulse transmit waveform stored in the digital memory comprise a sequence of one-bit digital words.

11. The beamformer system of claim 9, wherein the digital samples of a pulse transmit waveform stored in the digital memory comprise a sequence of three-bit digital words.

12. The beamformer system of claim 1, wherein the digital memory is adapted to be addressed simultaneously by a plurality of channel address counters.

13. The beamformer system of claim 1, wherein the channel address counters are further adapted to address different sequences of digital samples of different transmit waveforms for the common transmit event.

14. The beamformer system of claim 1, wherein the samples of a plurality of transmit waveforms comprise pulse transmit waveforms of a same fundamental pulse frequency and differing pulse widths.

* * * * *